United States Patent [19]

Nelson

[11] Patent Number: 4,999,447

[45] Date of Patent: Mar. 12, 1991

[54] PREPARATION OF ALKYL SILANES

[75] Inventor: Gunner E. Nelson, Baton Rouge, La.

[73] Assignee: Ethyl Corporation, Richmond, Va.

[21] Appl. No.: 346,232

[22] Filed: May 1, 1989

Related U.S. Application Data

[63] Continuation-in-part of Ser. No. 198,514, May 24, 1988, Pat. No. 4,916,245, and Ser. No. 129,001, Dec. 3, 1987, Pat. No. 4,845,260, which is a continuation-in-part of Ser. No. 17,852, Feb. 24, 1987, Pat. No. 4,711,965.

[51] Int. Cl.$^5$ .............................................. C07F 7/08
[52] U.S. Cl. .................................................... 556/478
[58] Field of Search ........................................ 556/478

[56] References Cited

U.S. PATENT DOCUMENTS

| | | | |
|---|---|---|---|
| 2,857,414 | 10/1958 | Schmidt et al. | 260/448.2 |
| 3,036,132 | 5/1962 | Becker | 556/478 UX |
| 3,398,171 | 8/1968 | Giraitis et al. | 260/448.2 |
| 4,367,343 | 1/1983 | Tamborski et al. | 556/478 |
| 4,595,777 | 6/1986 | Bakshi et al. | 556/478 |
| 4,683,321 | 7/1987 | Nelson | 556/478 |
| 4,711,965 | 12/1987 | Nelson | 556/478 |
| 4,711,966 | 12/1987 | Nelson | 556/478 |

FOREIGN PATENT DOCUMENTS 825987 12/1959 United Kingdom .
900132 7/1962 United Kingdom .

OTHER PUBLICATIONS

Tamborski et al, *Ind. Eng. Chem. Prod. Res. Dev.* 22, 172–178 (1983), Synthesis & Prop. of Silahydrocarbons, A Class of Therm. Stable, Wide Liquid Range Fluids.
Ashby et al, *Inorg. Chem.* 2, No. 3, pp. 499–504 (1963).
Zaharkin et al, *Izvestiya Akademii Nauk SSSR, Seriya Khimicheskaya* No. 1, pp. 142–143 (Jan. 1966).
Gavrilenko et al., *Zhurnal Obschchei Khimii* 39, No. 5, pp. 1055–1058 (May 1969).

*Primary Examiner*—Paul F. Shaver
*Attorney, Agent, or Firm*—John F. Sieberth; Terry B. Morris

[57] ABSTRACT

Olefins and metal aluminum tetraalkyls react with alkylhalosilanes to yield mixtures of tetraalkyl silanes which may be employed as functional fluids. For example, decene-1 and sodium aluminum tetraoctyl, $NaAl(C_8H_{17})_4$, react with dialkyldichlorosilane. The mole ratio of sodium aluminum tetraalkyl to halosilane in from about 0.5:1.0 to about 1:1, and the ratio of olefin to the metal aluminate is selected to confer in the product mixture, the desired concentration of alkyl radicals derived from the olefin.

20 Claims, No Drawings

PREPARATION OF ALKYL SILANES

CROSS-REFERENCE TO RELATED APPLICATIONS AND PATENTS

This application is a continuation-in-part of application Ser. No. 198,514, filed May 24, 1988, now U.S. Pat. No. 4,916,245, and of application Ser. No. 129,001, filed Dec. 3, 1987, now U.S. Pat. No. 4,845,260, which in turn is a continuation-in-part of application Ser. No. 17,852, filed Feb. 24, 1987, now U.S. Pat. No. 4,711,965. This application is related to U.S. Pat. No. 4,711,966, which issued in my name on Dec. 8, 1987.

FIELD OF THE INVENTION

This invention relates to the reaction of olefins and alkali metal aluminum tetraalkyls (also known as alkali metal aluminates) with alkyl halosilanes. This invention is particularly directed to preparation of tetraalkylsilane mixtures produced by this reaction. Such mixtures are useful as functional fluids.

BACKGROUND OF THE INVENTION

Methods for the synthesis of tetraalkyl silanes include the reaction of alkyl magnesium halides or alkyl lithiums with halosilicon compounds; Tamborski et al U.S. Pat. No. 4,367,343, and Tamborski et al, "Synthesis and Properties of Silahydrocarbons, A Class of Thermally Stable, Wide Liquid Range Fluids", *Ind. Eno. Chem. Prod. Res. Dev.* 22, 172–178 (1983).

British patent 825,987 to Kali-Chemie AG discloses the reaction of trialkyl aluminums with alkyl- or arylchlorosilanes.

Jenkner, British patent 900,132, (also to Kali-Chemie) pertains to the reaction of sodium aluminum tetraethyl with halosilanes, such as silicon tetrachloride, with the reactants in a ratio of 4 to 1.

Bakshi et al, U.S. Pat. No. 4,595,777 pertains to the process of reacting an alkylchlorosilane with a trialkylaluminum.

Giraitis et al, U.S. Pat. No. 3,398,171, relates to the reaction of organosilanes and mixed metal compounds ANR$_n$ Wherein A is an alkali metal and M can be aluminum. The process is conducted at a reaction temperature of $-20°$ C. to $+50°$ C. and uses a higher mole ratio of reactants than utilized in this invention (compare the paragraph bridging Columns 5 and 6 of the reference patent with the description of this invention given below).

SUMMARY OF THE INVENTION

This invention pertains to the preparation of tetraalkylsilanes, wherein one or two alkyl groups are comparatively small and the other two or three are comparatively large. The small alkyl groups preferably have from one to about four carbon atoms, while the larger groups preferably have from about 8 to about 14 carbon atoms each. These products are prepared by a process which comprises reacting an alkali metal aluminum tetraalkyl, MAlR'$_4$, and an olefin corresponding to R', with an alkyl halosilane, RSiX$_3$ or R$_2$SiX$_2$. In the above formulas, each X is a halide radical, R is the smaller alkyl group (preferably one to about four carbons), and R' is the larger alkyl group. The process is conducted such that about 2 to about 4 moles of metal tetraalkyl are reacted with each 4 mole portion of alkyl halosilane employed.

More particularly, in the process of this invention one equivalent of MAlR'$_4$ reactant combines with one equivalent of alkylhalosilane reactant. In order to assist the reaction through the effect of mass action, an excess of up to about one additional equivalent of R' radical as MAlR'$_4$ can be utilized in the reaction mixture. For the process of this invention, one does not use a very large excess of MAlR'$_4$ reactant, since such excesses can cause the reaction to take a different course, which for the purpose of this invention is not desired; confer, Jenkner, and Giraitis et al, supra.

As indicated above, an olefin reactant corresponding to R', is used in the process of this invention, in order to provide a portion of the larger alkyl radicals in the product produced.

In a highly preferred embodiment, the alkyl radical R' corresponding to the olefin differs from any of the alkyl radicals in the alkali metal aluminum tetraalkyl. By use of this preferred embodiment, a product mixture can be obtained which contains alkyl groups from the aluminum compound, as well as a dissimilar alkyl group produced from the olefin. Product mixtures produced in this way can have a composition selected to have one or more desired properties. In other words, the product composition can be 'tailor-made' by selecting (a) the type and concentration of the alkyl groups within the aluminum tetraalkyl, and (b) the olefin reactant.

Although the mechanism of the process of this invention is not known in detail, it is believed that the olefin reactant does not react directly with the alkyl halosilane. More particularly, it appears that the olefin first forms an unidentified reaction intermediate containing aluminum, which reacts with the alkyl halosilane.

In my prior patent U.S. Pat. No. 4,711,965, cited above, I described a reaction in which a mixture of sodium aluminum tetraalkyls is reacted with an alkyl halosilane to produce a mixture of tetrahydrocarbylsilane products. In the process of the invention described in this application, it is not necessary to use a mixture of sodium aluminum tetraalkyls in order to prepare a mixed tetrahydrocarbylsilane product. Instead, one may use just one sodium aluminum tetraalkyl, and employ an olefin in place of the second aluminum tetraalkyl. The ability to replace one alkali metal aluminum tetraalkyl with an olefin in the process of my prior patent is entirely unexpected.

The process of this invention is simple, and has decided advantages. For example, with the process of the instant invention, it is unnecessary to make a second aluminum tetraalkyl compound. Secondly, storage of metal aluminum tetraalkyl reactants is simplified, since only one aluminum tetraalkyl needs to be stored for subsequent reaction, rather than two. Furthermore, with the process of this invention, a whole family of different products can be made from one alkali metal aluminum tetraalkyl. More specifically, a family of products can be made by reacting the selected tetraalkyl with different, selected olefins.

Although a preferred embodiment of this invention comprises the reaction of an alkyl halosilane with one alkali metal aluminum tetraalkyl and one olefin, it is to be understood that this invention comprises processes in which more than one metal aluminate and/or olefin are employed as reactants.

Products of this invention are useful as functional fluids, with such diverse suggested uses as engine lubrication, electrical insulation, and as heat transfer media. They can also be used as hydraulic fluids. The products of this invention are particularly useful under high temperature conditions where petroleum-based or synthetic hydrocarbon-based fluids cannot meet specifications. Product mixtures can be made to achieve desired rheological properties.

DESCRIPTION OF PREFERRED EMBODIMENTS

In a highly preferred embodiment, this invention comprises a process for the preparation of a mixture of tetraalkylsilanes having the formula $RSiR'_3$ or $R_2SiR'_2$ wherein R and R' are alkyl radicals, the radicals depicted by R' are alike or different, R has from 1 to about 4 carbon atoms, and R' has from about 8 to about 14 carbon atoms; said process comprising contacting reactants (a), (b) and (c) at a reaction temperature, wherein:

reactant (a) is an alkali metal aluminum tetraalkyl having the formula $MAlR'_4$ wherein M is an alkali metal selected from the class consisting of lithium, sodium, and potassium, and R' has the same significance as above, reactant (b) is an alkylhalosilane silane having the formula $RSiX_3$ or $R_2SiX_2$, wherein each X is a halogen radical selected from fluoride, chloride, and bromide, and R has the same significance as above, and reactant (c) is an olefin to which an alkyl radical R' corresponds, wherein R' has the same significance as above, such that the mole ratio of reactant (a) to reactant (b) is from about 0.5:1.0 to about 1:1, and the ratio of reactant (c) to reactant (a) is selected to confer in said product mixture of tetraalkylsilanes, the desired concentration of radicals R' derived from said olefin.

As stated above, the process of this invention comprises a reaction of an alkali metal aluminate, $MAlR'_4$. Lithium, sodium and potassium aluminates can be used, with the lithium and sodium compounds being preferred. The sodium aluminates are highly preferred for reasons of economics and availability. Preferably, each radical indicated by R' in the formula $MAlR'_4$ is a hydrocarbyl, straight chain alkyl radical of about 8 to about 14 carbon atoms; however, it is to be understood that the radicals need not be limited to this structural configuration, and the size of the radicals can be larger or smaller than those within the preferred range.

The radicals of the preferred configuration and size appear to yield the more useful products, and they are preferred for that reason. However, any metal aluminate $MAlR'_4$ can be used for the process of this invention, so long as the radicals depicted by R' are stable under the reaction conditions employed, do not form an untoward amount of undesirable co-product when subjected to the reaction conditions employed, or unduly retard the reaction because of steric hindrance.

As mentioned above, the metal aluminate reactant may contain one or more groups indicated by R'. Alternatively, a mixture of metal aluminates can be used. The metal aluminate or aluminates need not be pure; for example, an aluminate can be used in the reaction mixture in which it is formed. Thus for example, Na, Al, and $H_2$ can be reacted in a hydrocarbon to form $NaAlH_4$, and the $NaAlH_4$, unisolated or isolated, can be reacted with an olefin, such as octene-1, or a mixture of olefins, such as octene-1 and decene-1 in a mole ratio of 2 to 1, and the resultant reaction mixture used as a reactant in the process of this invention. When the reactant is formed in this way, the olefin is generally used in excess. Consequently, the metal aluminate reactant used in the instant process can frequently be admixed with an olefin, or mixture of olefins from which the metal aluminate is prepared. Accordingly, the number of moles of olefin available for reaction in the metal aluminate reactant is the sum of moles of olefin in the metal aluminate plus moles of unreacted olefin admixed with the metal aluminate.

The metal aluminate reactant can be formed in situ by (a) reacting an alkali metal with aluminum, hydrogen and olefin in the presence of an organoaluminum catalyst, and (b) adding additional catalyst to the reaction mixture during the reaction to insure formation of the metal aluminate reactant, $MAlR'_4$. Use of such procedures is illustrated in my prior copending application Ser. No. 129,001, filed Dec. 3, 1987, all disclosure of which is incorporated herein by reference.

An olefin is intentionally added as a reactant to the reaction mixture employed in the process of this invention. In a highly preferred embodiment, the olefin(s) added are different from the olefin(s) employed to make the metal aluminate. The amount of olefin added as a reactant is selected to confer in the product mixture, the desired concentration of R' radicals derived from the olefin. For example, one may use a mixture of 1.5 moles of olefin and 0.75 mole of sodium aluminum tetraalkyl reactant. When this mole ratio is employed, the mole ratio of alkyl groups in the mixture of hydrocarbylsilanes produced will have the ratio of 2:1. In other words, there will be twice as many moles of R' radicals conferred by the metal aluminate reactant as contributed by the olefin. In general, one may use a mole ratio of olefin to metal aluminate reactant within the range of 2:1 to 20:1. Greater or lesser amounts may be used, if desired for there is no real upper or lower limit to the amount of olefin which can be employed. However, a large excess of olefin reactant may not be feasible since it takes up a considerable portion of the reactor space. If a product distribution is desired which requires an undesirable amount of olefin reactant, my process disclosed in U.S. Pat. No. 4,711,965, is preferred.

Thus, the process of this invention can be considered to have a significant, advantageous relationship with the process of U.S. Pat. No. 4,711,965, infra. As discussed above, in some instances the process of the instant invention is advantageous since it obviates the need to employ a mixture of alkali metal aluminate reactants. On the other hand, in some instances the process of my prior patent is advantageous, since it obviates the need to employ an undesirably large amount of olefin reactant.

Of course, instead of using two metal aluminates and the process of my aforementioned patent, one may employ the process of this invention using a different olefin/metal aluminate mixture, and thereby eliminate the need for a large amount of olefin reactant. For example, instead of using sodium aluminum tetraoctyl and an undesirably large amount of decene-1, one may use the process of this invention and 'switch' the reactants, i.e. react sodium aluminum tetradecyl and octene-1 (with the alkyl halosilane). By changing the reactants in this way, a large relative amount of olefin can be eliminated.

The process described herein can be used to make product mixtures which are the same as or related to the product mixtures produced by the methods disclosed in U.S. Pat. No. 4,711,965, and 4,711,966. Examples of olefins which can be employed in the process of this invention are mentioned in the paragraph below.

Most olefins available in large commercial quantities are made from natural products or by chain growth of ethylene. In either case, the olefin usually has an even number of carbon atoms. However, it is to be understood that an even number of carbon atoms is not critical, and the olefin and MAlR'$_4$ reactants can correspond to or have R' radicals with an odd number of carbon atoms. Nevertheless, because of the more ready availability of even numbered olefins, the preferred MAlR'$_4$ reactants for this invention have alkyl radicals (depicted by R') that are derived from one or more of the following olefins:

octene-1
decene-1
dodecene-1
tetradecene-1
hexadecene-1

Such olefins are also preferred reactants for this invention.

The other reactant employed in the process of this invention is an alkyl trihalosilane, RSiX$_3$. In this reactant, R is a lower alkyl radical such as methyl, ethyl, propyl, butyl, isopropyl, sec-butyl or the like. Preferably, R is unbranched. More preferably, R is methyl. The three groups indicated by X are halide radicals; preferably all three are the same; however, reactants with two or three halo groups per molecule can be used. Reactants with two halo groups per molecule have the formula R$_2$SiX$_2$. In these reactants, R is a lower alkyl radical such as methyl, ethyl, propyl, butyl, isopropyl, sec-butyl or the like. Preferably, R is unbranched. More preferably, R is methyl. Preferably, the halide groups are chloro or bromo radicals, most preferably they are all chloro groups. Although alkyl halosilanes in which the alkyl group has from 1 to 4 carbon atoms are preferred, it is to be understood that one may use as a reactant a compound having the formula R''SiX$_3$ or R''$_2$SiX$_2$ wherein R'' is an alkyl group that has 5 or more carbon atoms.

The process of this invention is conducted using a reaction temperature that is high enough to cause the reaction to take place at a reasonable rate, but not so high that it causes an undesirable amount of side reaction or decomposition to occur. Generally speaking, a temperature above 150° C. and below 230° C. is used. Preferably, the temperature is from about 180° C. to 230° C.

The reaction time is not a truly independent variable but depends at least to some extent on the other reaction conditions employed such as the reaction temperature. Generally speaking, reaction is essentially complete in from about 3 to 10 hours with 5 to 6 hours being typical.

The reaction pressure does not have a large effect on the course of the reaction. Atmospheric, sub-atmospheric and super atmospheric pressure can be used. Atmospheric pressure or the autogenous pressure of the system is preferred.

Although the process of this invention is preferably conducted using alkali metal aluminates, MAlR'$_4$, such as described above, it is to be borne in mind that similar reactants can also be used in this invention in substantially the same way, to produce substantially the same results. Thus for example, one may use alkaline earth aluminates, M'(AlR'$_4$)$_2$, wherein M' is Mg, Ca or Ba. When these materials are used in the process of this invention, one-half of the molar quantities described above for MAlR'$_4$ reactants are employed, since each molecule of the alkaline earth compounds contains two, i.e. twice as many, (AlR'$_4$) groups.

EXAMPLE 1

To a 1 liter autoclave was charged 172.4 grams of a sodium aluminum tetradecyl NaAl(C$_{10}$H$_{21}$)$_4$ solution consisting essentially of 167.2 millimoles of sodium aluminum tetradecyl and 334 5 millimoles of decene. The total number of moles of C$_{10}$ alkyl groups available for bonding was equal to [(4×167.2)+334.5] or 1003.3 millimoles. There was also charged 74.98 grams of octene-1 (668.9 millimoles). The mole fraction of octene-1 was equal to 0.40.

The autoclave was also charged with 29.4 grams of methyl trichlorosilane (196.7 millimoles).

The reaction mixture was heated at 190° C. for 5 hours. It was then cooled, and hydrolyzed by slow addition to 750 milliliters of 15 percent caustic solution. The hydrolysis was conducted using rapid agitation. After hydrolysis, the organic phase was washed with caustic, and then several times with water.

The organic phase was stripped under vacuum to remove excess olefin reactant and vinylidene olefin produced as a by-product. There was obtained a 94 percent yield of a silahydrocarbon mixture having the following composition:

| Component | Mole Fraction | Calculated Mole Fraction |
|---|---|---|
| 1. CH$_3$Si(C$_8$H$_{17}$)$_3$ | 0.069 | 0.064 |
| 2. CH$_3$Si(C$_8$H$_{17}$)$_2$(C$_{10}$H$_{21}$) | 0.281 | 0.288 |
| 3. CH$_3$Si(C$_8$H$_{17}$)(C$_{10}$H$_{21}$)$_2$ | 0.420 | 0.432 |
| 4. CH$_3$Si(C$_{10}$H$_{21}$)$_3$ | 0.230 | 0.216 |

The calculated mole fraction set forth above is derived from the relationship $(a+b)^3$, i.e.:

$$a^3 + 3a^2b + 3ab^2 + b^3$$

wherein a is the mole fraction of one alkyl component, and b is the mole fraction of the other alkyl component. The mole fraction of one component is equal to the number of moles of that component divided by the sum of the number of moles of both alkyl components available for bonding. As indicated above, the number moles of alkyl component in one case is equal to the number of moles of alkyl groups present in the sodium tetraalkyl aluminate reactant, plus the number of moles of excess olefin admixed with that reactant. For the other component, the number of moles of alkyl groups available for bonding is equal to the number of moles of olefin employed as reactant (c).

EXAMPLE 2

A 160 gram portion of metal aluminate solution used in the preceding example was stripped at a temperature below 75° C. and at a pressure of 3 mm Hg. The stripped solution contained 94.7 grams of NaAl(C$_{10}$H$_{21}$)$_4$ and 10.9 grams of decene-1. This mixture was charged to a 1 liter reactor with 156.4 grams of octene-1, 40 grams of heptane, and 27.3 grams of methyl trichlorosilane (182 millimoles).

The total C$_{10}$ alkyl available was 699 millimoles, and the total C$_8$ alkyl available was 1396.4 millimoles. The mole fraction of C$_8$ alkyl was 0.666.

The reaction mixture was heated and then worked up as in Example 1. Gas chromatographic analysis indicated that a 91.5 percent yield of a mixture of products was obtained. The product mixture was as follows:

| Component | Mole Fraction | Calculated Mole Fraction |
|---|---|---|
| 1. $CH_3Si(C_8H_{17})_3$ | 0.22 | 0.30 |
| 2. $CH_3Si(C_8H_{17})_2(C_{10}H_{21})$ | 0.41 | 0.44 |
| 3. $CH_3Si(C_8H_{17})(C_{10}H_{21})_2$ | 0.28 | 0.22 |
| 4. $CH_3Si(C_{10}H_{21})_3$ | 0.09 | 0.04 |

The process of this example can be extended to the use of lithium and potassium aluminum tetraalkyls in which the alkyl groups are octyl, decyl, dodecyl or tetradecyl. Such substances may be reacted with methyl, ethyl, n-propyl, isopropyl, or n-butyl trichlorosilane or the trifluoro or tribromo analogs of these substances in the presence of an olefin selected from octene-1, decene-1, dodecene-1, and tetradecene-1. The reaction can be conducted at exogenous pressure or at pressures of up to 500 psi or higher. Such elevated pressures may be imposed by use of an inert gas atmosphere, e.g. nitrogen or argon. The reactions can be conducted at 180° C. to 230° C. for 3 to 10 hours. The mole ratio of metal aluminate to trihalosilane may be in the range of about (0.75:1.0) to (1.0:1.0). The mole ratio of added olefin (i.e. the olefin added as a reactant and not including any olefin present with the sodium tetraalkyl aluminate) can be in the range of from (1:2) to (1:20).

EXAMPLE 3

To a 1 liter autoclave was charged 163 grams of a solution containing 214.3 millimoles of sodium tetraoctyl aluminate, $NaAl(C_8H_{17})_4$, and 495 millimoles of octene-1. The autoclave was also charged with 113.5 grams of decene-1 (811 millimoles) and 37.7 grams of methyl trichlorosilane.

The total $C_8$ alkyl available was equal to $[(4 \times 214.3) + 495]$, and the mole fraction of $C_8$ alkyl was 0.625.

Reaction and workup, as in the previous examples, result ed in an 84.1 percent yield of product having the following composition:

| Component | Mole Fraction | Calculated Mole Fraction |
|---|---|---|
| 1. $CH_3Si(C_8H_{17})_3$ | 0.40 | 0.24 |
| 2. $CH_3Si(C_8H_{17})_2(C_{10}H_{21})$ | 0.41 | 0.44 |
| 3. $CH_3Si(C_8H_{17})(C_{10}H_{21})_2$ | 0.17 | 0.26 |
| 4. $CH_3Si(C_{10}H_{21})_3$ | 0.03 | 0.05 |

The sodium aluminum tetraoctyl in this and the following example was prepared using tri-n-octylaluminum as a catalyst, while the aluminate used in Examples 1 and 2 was prepared using lithium aluminum hydride as a catalyst. It will be noted that the mole fractions found in Examples 1 and 2 more closely conform to the calculated mole fractions than the mole fractions in Examples 3 and 4. The reason for the disparity in activity between the two types of metal aluminates is unknown. The disparity in activity is also unexpected.

With regard to the preparation of the tetraalkyl aluminate reactant, it is known in the art that lithium aluminum hydride reacts with olefins at about 110°-120° C. forming complexes with the structure $LiAlR_4$. Sodium aluminum hydride is not added to olefins even at 180° C. without the presence of catalytic amounts of a material selected from trialkyl aluminums, dialkyl aluminum hydrides, lithium aluminum hydride, or aluminum, zinc or lithium halide. The first three hydrogens are readily replaced at 80°-130° C., but the fourth requires a temperature of 170°-230° C. or thereabouts, for about 3 to 6 hours. The process is preferentially conducted in the presence of an excess of olefin, e.g. a 1:8 mole ratio of $NaAlH_4$ to olefin, and 5-15 mole % (based on $NaAlH_4$) of the catalyst. A paraffin diluent can be used in the reaction mixture.

As an illustration of the preparation of $NaAlR'_4$, a reactor is charged with $NaAlH_4$, catalyst, and olefin, and heated for 1-2 hours at 125° C., followed by 3-4 hours at 175° C. (It is believed the duration of the heating cycle can be reduced somewhat.) The product is discharged after cooling. The final product typically contains 30-65% of $NaAlR_4$, and is suitable for most reactions. It is not necessary that the aluminate be employed in the product mix; if desired it can be isolated from some or all of the other substances present in the resultant reaction mixture.

EXAMPLE 4

To a 1 liter autoclave was charged 290.8 grams of an octene-1 solution containing 382 millimoles sodium aluminum tetraoctyl. The total $C_8$ alkyl available from the metal aluminate and the octene-1 solvent was 2,412 millimoles. There was also added to the autoclave 169 grams of decene-1, i.e. 1,206 millimoles. The mole fraction of $C_8$ alkyl was 0.666. Methyl trichlorosilane, 67.2 grams (450 millimoles) was also charged to the reaction vessel.

Reaction and workup, as before, resulted in an 89.8 percent yield of a product which was shown to have the following composition:

| Component | Mole Fraction | Calculated Mole Fraction |
|---|---|---|
| 1. $CH_3Si(C_8H_{17})_3$ | 0.40 | 0.30 |
| 2. $CH_3Si(C_8H_{17})_2(C_{10}H_{21})$ | 0.43 | 0.44 |
| 3. $CH_3Si(C_8H_{17})(C_{10}H_{21})_2$ | 0.15 | 0.22 |
| 4. $CH_3Si(C_{10}H_{21})_3$ | 0.02 | 0.04 |

EXAMPLE 5

In this example, a solution of sodium aluminum tetraoctyl prepared using lithium aluminum hydride as a catalyst was employed. The total solution was 131 grams. Each milliliter contained 1.3036 millimoles of sodium aluminum tetraoctyl and 3.085 millimoles of octene-1. The total $C_8$ alkyl available was equal to $[4 \times 1.3036) + 3.085] \times 131$, or 1,087.2 millimoles.

The reaction vessel was also charged with 76.1 grams (543.7 millimoles) of decene-1 and 30 grams (200.9 millimoles) of methyl trichlorosilane.

The mole fraction of $C_8$ alkyl available was 0.667.

Reaction and workup, as before, resulted in a 92.1 percent yield of product which, as in the previous examples, was shown by gas chromatography to have the following distribution:

| Component | Mole Fraction | Calculated Mole Fraction |
|---|---|---|
| 1. $CH_3Si(C_8H_{17})_3$ | 0.36 | 0.30 |
| 2. $CH_3Si(C_8H_{17})_2(C_{10}H_{21})$ | 0.42 | 0.44 |
| 3. $CH_3Si(C_8H_{17})(C_{10}H_{21})_2$ | 0.19 | 0.22 |

-continued

| | Component | Mole Fraction | Calculated Mole Fraction |
|---|---|---|---|
| 4. | $CH_3Si(C_{10}H_{21})_3$ | 0.03 | 0.04 |

EXAMPLE 6

To a 1 liter autoclave was charged 170.8 grams of a solution of NaAl(n-octyl)$_4$ in octene-1/heptane, assaying 3.32% aluminum. (Therefore total aluminate was 210 millimoles. Total $C_8$ present was 1231 millimoles: 840 millimoles bound on aluminum plus 391 millimoles present as free olefin.)

Also charged to the autoclave were 616 millimoles of decene-1 (giving a ratio $C_8/C_{10}$ of 2/1); 323 millimoles of $(CH_3)_2SiCl_2$ (giving a ratio Al/Si of 0.65/1); and 100 milliliters of n-heptane.

This reaction mixture was heated at 190° C. for 6 hours, after which the vessel was cooled. The liquid phase was decanted from the solid NaAlCl$_4$ phase and hydrolyzed by addition to 1 liter of vigorously agitated 15% NaOH. The organic phase was separated, washed with 500 millimoles of 15% NaOH and then with successive portions of water until the washings were neutral to litmus. After drying over MgSO$_4$, residual light olefins were removed under vacuum, yielding 79.3 grams of water-white product which was analyzed by GLC.

Purity was determined by GLC to be 94.35%, the remainder being $C_{18}$ and $C_{20}$ olefins. The overall yield was 76.7%. The composition of the product was as follows:

| | Component | Mole Fraction | Calculated Mole Fraction |
|---|---|---|---|
| 1. | $(CH_3)_2Si(C_8H_{17})_2$ | 0.488 | 0.44 |
| 2. | $(CH_3)_2Si(C_8H_{17})(C_{10}H_{21})$ | 0.388 | 0.44 |
| 3. | $(CH_3)_2Si(C_{10}H_{21})_2$ | 0.124 | 0.11 |

EXAMPLE 7

An aluminate was prepared from NaAlH$_4$ and a 2/1 (mole ratio) mixture of 1-octene and 1-decene in 100% excess. A portion of this solution, containing 470.9 millimoles of aluminate, was reacted with 780 millimoles of $(CH_3)_2SiCl_2$ in an autoclave, heating with vigorous stirring at 190° C. for five hours.

After cooling, the organic phase was decanted from the solid NaAlCl$_4$ phase and discharged into one liter of vigorously stirred 15% caustic solution. It was washed once with caustic solution and several times with water, then dried over MgSO$_4$. Low boiling components of the product mixture were removed under vacuum leaving 179.5 g of the desired material as bottoms.

GLC analysis of the dried solution showed a 4/4/1 (mole ratio) mixture of the following:

$(CH_3)_2Si(C_8H_{17})_2$,
$(CH_3)_2Si(C_8H_{17})(C_{10}H_{21})$, and
$(CH_3)_2Si(C_{10}H_{21})_2$.

The yield based on $(CH_3)_2SiCl_2$ was 77.6%. The product melted at $-45°$ C. The viscosity at 40° C. was 4.77 centistokes, and the viscosity at 100° C. was 1.70 centistokes.

Products of this invention are useful as functional fluids, e.g. hydraulic fluids for military or other applications. Hydraulic fluids are used in hydraulic systems to transmit pressure or energy. They also serve to reduce friction in bearings and between sliding surfaces in pumps and similar articles. Hydraulic and other functional fluids also protect surfaces from rusting, and can remove undesirable particulate matter away from surfaces.

Like other functional fluid base stocks, the silahydrocarbons produced by the process of this invention can be admixed with additives such as rust inhibitors, antiwear agents, corrosion inhibitors and the like.

It is to be understood that modification of the above described invention can be made without departing from the spirit and scope of the following claims.

I claim:

1. A process for the preparation of a mixture of tetraalkylsilanes, said process comprising contacting reactants (a), (b), and (c) at a reaction temperature, wherein:

reactant (a) is an alkali metal aluminum tetraalkyl having the formula MAlR'$_4$ wherein M is an alkali metal selected from the class consisting of lithium, sodium, and potassium, R' is an alkyl radical having from about 8 to about 14 carbon atoms, and the radicals depicted by R' are alike or different:

reactant (b) is an alkylhalosilane having two halo groups per molecule selected from fluoride, chloride, and bromide, and each alkyl group having from 1 to about 4 carbon atoms; and reactant (c) is an olefin to which an alkyl radical R' corresponds, wherein R' has the same significance as above;

such that the mole ratio of reactant (a) to reactant (b) is from about 0.5:1.0 to about 1:1, and the ratio of reactant (c) to reactant (a) is selected to confer in said product mixture of tetraalkylsilanes, the desired concentration of alkyl radicals derived from said olefin.

2. A process of claim 1, wherein said reaction temperature is from about 150° C. to about 230° C.

3. A process of claim 2, wherein said temperature is from about 180° C. to about 230° C.

4. A process of claim 1, wherein said alkali metal aluminum tetraalkyl has the formula NaAlR'$_4$, wherein the 4 alkyl radicals represented by R' are the same.

5. The process of claim 4, wherein said alkali metal aluminum tetraalkyl is sodium aluminum tetraoctyl.

6. A process of claim 1, wherein said reactant (b) is methyltrichlorosilane.

7. A process of claim 1, wherein said reactant (b) is dimethyldichlorosilane.

8. A process of claim 1, wherein said reactant (c) is decene-1.

9. A process of claim 1, wherein said reactant (c) is a mixture of octene-1 and decene-1.

10. A process of claim 1, wherein about 0.75 mole of reactant (a) is employed for each mole of reactant (b), and per each mole of reactant (b) about 1.5 mole of reactant (c) is employed, such that the ratio of alkyl radicals in said product mixture of tetraalkylsilanes, derived from reactant (c) and reactant (a), is about 2:1.

11. A process for the preparation of a mixture of tetraalkylsilanes, said process comprising contacting reactants (a), (b), and (c) at a reaction temperature, wherein:

reactant (a) is an alkali metal aluminum tetraalkyl having the formula MAlR'$_4$ wherein M is an alkali metal selected from the class consisting of lithium, sodium, and potassium, R' is an alkyl radical having from about 8 to about 14 carbon atoms, and the radicals depicted by R' are alike or different;

reactant (b) is an alkylhalosilane having two halo groups per molecule selected from fluoride, chloride, and bromide, and each alkyl group having from 1 to about 4 carbon atoms; and reactant (c) is an olefin to which an alkyl radical R' corresponds, wherein R' has the same significance as above;

such that the mole ratio of reactant (a) to reactant (b) is from about 0.5:1.0 to about 1:1, and the ratio of reactant (c) to reactant (a) is selected to confer in said product mixture of tetraalkylsilanes, the desired concentration of alkyl radicals derived from said olefin.

12. A process of claim 11 wherein said reaction temperature is from about 150° C. to about 230° C.

13. A process of claim 12 wherein said temperature is from about 180° C. to about 230° C.

14. A process of claim 11, wherein said alkali metal aluminum tetraalkyl has the formula a NaAlR'$_4$, wherein the 4 alkyl radicals represented by R' are the same.

15. A process of claim 14, wherein said alkali metal aluminum tetraalkyl is sodium aluminum tetraoctyl.

16. A process of claim 11, wherein said reactant (b) is dimethyldichlorosilane.

17. A process of claim 11, wherein said reactant (c) is decene-1.

18. A process of claim 11, wherein said reactant (c) is a mixture of octene-1 and decene-1.

19. A process of claim 11 wherein about 0.75 mole of reactant (a) is employed for each <mole of reactant (b), and per each mole of reactant (b) about 1.5 mole of reactant (c) is employed, such that the ratio of alkyl radicals in said product mixture of tetraalkylsilanes, derived from reactant (c) and reactant (a), is about 2:1.

20. A process of claim 1, wherein said alkali metal aluminum tetraalkyl is formed in situ.

* * * * *